United States Patent [19]

Hasegawa et al.

[11] Patent Number: 4,966,985
[45] Date of Patent: Oct. 30, 1990

[54] OPTICALLY ACTIVE CARBOALKYLATED AMINO ALCOHOLS AND THEIR UTILIZATION IN OPTICAL RESOLUTION

[75] Inventors: Masaki Hasegawa, Tokyo; Kazuhiko Saigo, Souka; Yoichi Yuki; Kouzou Tachibana, both of Himeji, all of Japan

[73] Assignee: Daicel Chemical Industries, Ltd., Sakai, Japan

[21] Appl. No.: 946,460

[22] Filed: Dec. 24, 1986

[30] Foreign Application Priority Data

Dec. 27, 1985 [JP] Japan .................................. 60-293883
Dec. 27, 1985 [JP] Japan .................................. 60-293884

[51] Int. Cl.$^5$ ............................ C07F 1/08; C07F 3/06;
C07F 15/02; C07C 327/00
[52] U.S. Cl. ...................................... 556/116; 556/134;
556/148; 558/252; 560/39; 562/26; 562/444
[58] Field of Search ........................ 556/148, 116, 134;
558/252; 560/39; 562/444, 26; 260/502.6

[56] References Cited

U.S. PATENT DOCUMENTS

| | | | |
|---|---|---|---|
| 3,803,213 | 4/1974 | Weber et al. | 260/429 R |
| 4,529,713 | 7/1985 | Jouquey et al. | 562/444 X |
| 4,532,342 | 7/1985 | Hoefle et al. | 562/444 X |
| 4,619,984 | 10/1986 | Yuki et al. | 528/38 |

OTHER PUBLICATIONS

Chemisches Zentralblatt, vol. 140, No. 23, Jun. 4, 1969, pp. 127–128, Berlin K. Jankowski et al., Reaktionen von Epoxiden mit Glycin und seinen Derivaten, Canadian Journal of Chemistry, 1967, vol. 45(23), pp. 2865–2877. Journal of the American Chemical Society, vol. 108, No. 5, pp. 1103–1104, P. J. Sinclair et al., "Electrophilic Glycinates: New and Versatile Templates for Asymmetric Amino Acid Synthesis".

*Primary Examiner*—Paul F. Shaver
*Attorney, Agent, or Firm*—Flynn, Thiel, Boutell & Tanis

[57] ABSTRACT

A carboalkylated amino alcohol having each of the below shown formulae is novel and optically active. A separating agent comprising the alcohol and a support is effectively useful to separate a variety of racemates for example with chromatography. The alcohol may be chemically or physically combined with the support.

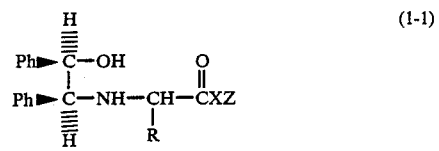

(1-1)

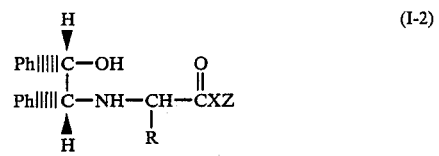

(1-2)

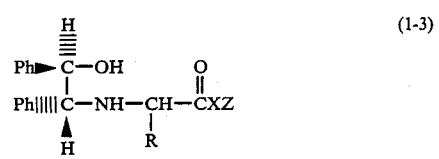

(1-3)

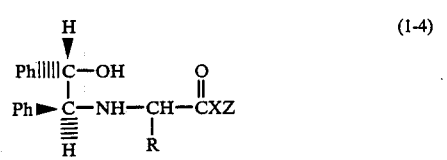

(1-4)

[wherein Ph represents a phenyl group, R represents a hydrogen atom, an alkyl group having the carbon number of 1 to 10, or an aryl group having the carbon number of 6 to 10, X represents an —O— group or a —S— group, and Z represents a hydrogen atom, an alkyl group having the carbon number of 1 to 10 or a metal element].

2 Claims, No Drawings

OPTICALLY ACTIVE CARBOALKYLATED AMINO ALCOHOLS AND THEIR UTILIZATION IN OPTICAL RESOLUTION

FIELD OF THE INVENTION

The present invention relates to novel optically active carboalkylated amino alcohols, separating agents comprising them, and a method for optical resolution.

In more detail, the present invention relates to novel optically active carboalkylated amino alcohol isomers, novel optically active separating agents consisting of a support and one of the optically active compounds, and a method for optical resolution by the novel separating agent. The novel separating agents in the present invention can be used as stationary phases for column chromatography which separates racemates The separating agent is called also an absorbent.

BACKGROUND OF THE INVENTION

It is known that for a conventional separating agent; in which an optically active compound is fixed on an inorganic support or an organic polymer support, natural amino acids are used as a source material of the optically active compound except for the following examples.

The exceptional examples are artificial amino acids such as phenylglycine and tertiary-leucine, basic and acidic compounds derived from natural amino acids and tartaric acid, and 1-arylethylamines. The exceptional examples are disclosed in the following literatures: Journal of Chromatography [V. A. Davankov et al, Vol. 82, page 352 (1973)]; Journal of Chromatography [C. Cubiron et al, Vol. 204, page 185 (1981)]; Chromatographia [V. A. Davancov et al, Vol. 13, page 677 (1980)]; Journal of High Resolution Chromatography and Chromatography Communication [G. Guvitz et al, Vol. 2, page 145 (1979)]. Moreover, examples using an basic compound, derived from an artificial or natural amino acid such as phenylglycine or tertiary-leucine, Journal of Chromatography [W. H. Pirkle et al, Vol. 192, page 143 (1980)] and Chromatographia [V. A. Davankov et al, Vol. 13, page 399 (1980)] are known.

The present inventors have accomplished the present invention as the result of various investigations on the improvement of the resolving ability of conventional separating agents in optical relolution. Namely, conventional separating agents having an optically active compound have been used as the stationary phases for column chromatography in order to resolve racemates optically. However, when a natural amino acid, an artifical amino acid, a basic or acidic compound derived from them, tartaric acid, or 1-arylethylamine is used as the optically active compound, the racemates that are possible to be optically resolved are limited. Therefore, a new chiral stationary phase, which can be applied to the optical resolution of wide-ranging racemates, is needed.

SUMMARY OF THE INVENTION

It is the primary object of the present invention to provide novel optically active carboalkylated amino alcohols represented by the following general formulae (1-1), (1-2), (1-3), and (1-4), respectively.

It is the second object of the present invention to provide novel optically active separating agents consisting of a support and one of the optically active compounds represented by the following general formulae (2-1), (2-2), (2-3) and (2-4), respectively.

It is the third object of the present invention to provide a method for the optical resolution of racemates.

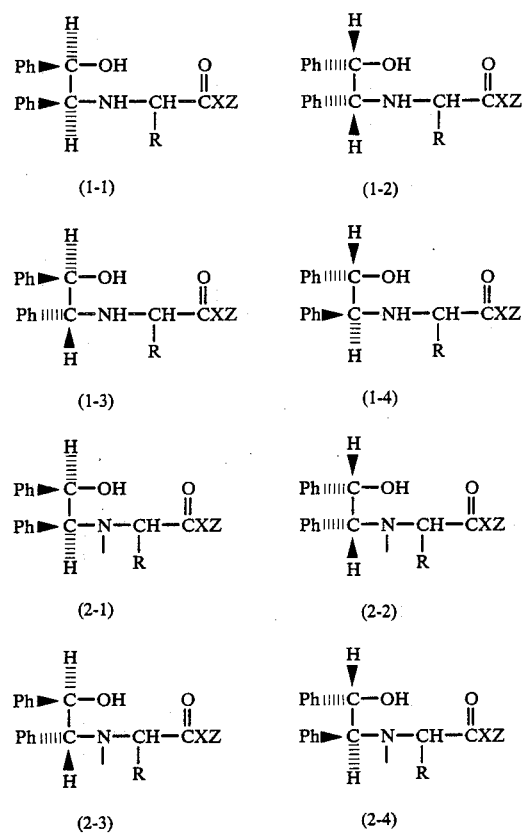

[wherein Ph represents a phenyl group, R represents a hydrogen atom, an alkyl group having the carbon number of 1 to 10, or an aryl group having the carbon number of 6 to 10, X represents an —O— group or a —S— group, and Z represents a hydrogen atom, an alkyl group having the carbon number of 1 to 10 or a metal element]

DETAILED DESCRIPTION OF THE INVENTION

The present inventors have investigated intensively to find out new optically active compounds applicable as reagents for asymmetric synthesis and/or separating agents for optical resolution, and have accomplished the present invention. The separating agent in the present invention can separate racemates which can not be separated by a conventional separating agent.

The first invention relates to novel optically active carboalkylated amino alcohols represented by the following general formulae (1-1), (1-2), (1-3) and (1-4).

The second invention relates to novel optically active separating agents consisting of a support and one of the optically active amino alcohols having the above shown formulae (2-1), (2-2), (2-3) and (2-4), respectively.

The third invention relates to a method for the optical resolution using the novel optically active separating agents.

The compositions of the present invention are described as follows.

The optically active carboalkylated amino alcohols in the first invention include the following concrete modes. Namely, R represents a hydrogen atom, an alkyl group having the carbon number of 1 to 10, or an aryl group having the carbon number of 6 to 10, X represents an —O— group or a —S— group, and Z represents a hydrogen atom, an alkyl group having the carbon number of 1 to 10 or a metal element in the general formulae (1), (1-2), (1-3) and (1-4).

More specifically, R represents a hydrogen atom, a methyl group, an ethyl group, a phenyl group, a tolyl group or a naphthyl group, the alkyl for Z is methyl or ethyl and the metal element is copper, zinc, nickel, iron, cobalt, magnesium, calcium, sodium, potassium, etc.

(Synthesis of optically active carboalkylated amino alcohols)

The optically active carboalkylated amino alcohols in the present invention can be prepared according to the following methods.

In the first method, erythro-2-amino-1,2-diphenylethanols, namely, (1S,2R)-2-amino-1,2-diphenylethanol [formula (3-1)] and (1R,2S)-2-amino1,2diphenylethanol [formula (3-2)] are used as a starting material. Moreover, threo-isomers, (1R,2R)-2-amino1,2-diphenylethanol [formula (3-3)] and (1S,2S)-2-amino-1,2-diphenylethanol [formula (3-4)], which can be converted from (1S,2R)- and (1R,2S)-forms, respectively, are also used as a starting material.

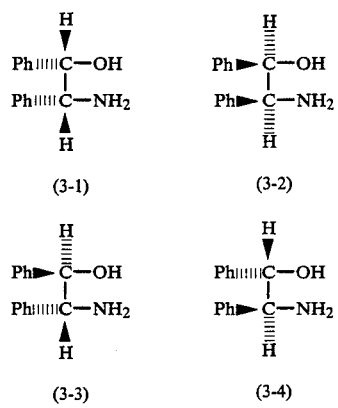

[wherein Ph represents a phenyl group]

Each optically active isomer described above is alkylated by a carbomethylating agent such as ethyl bromoacetate or by a carboalkylating agent such as ethyl 2-chloropropionate. Then, the ester part is converted to metallic salt such as sodium carboxylate or carbothiolate with sodium hydroxide or sodium hydrosulfide, respectively. Moreover, other metallic salts can be obtained via the corresponding carboxylic acid or carbothioic acid.

For example, when (1S,2R)-2-amino-1,2-diphenylethanol is alkylated with ethyl bromoacetate and converted to the sodium salt, the reaction steps are as shown in the following scheme.

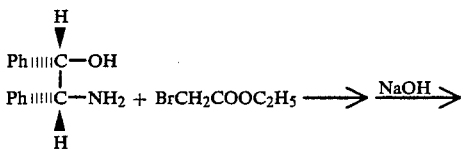

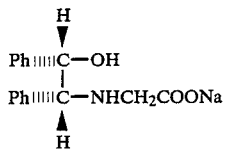

[wherein Ph represents a phenyl group]

In another method, racemic erythro-2-amino1,2-diphenylethanol or threo-2-amino-1,2-diphenylethanol is used as a starting material. Carboalkylation followed by hydrolysis gave racemic carboalkylated amino alcohol, which can be separated into the corresponding enatiomers by optical resolution.

Moreover, the optically active materials in the present invention can be synthesized not only by the methods described above but also by the ring-opening reaction of optically active trans-stilbene oxide with alkyl glycinate or alaninate followed by hydrolysis.

The precursors for the optically active materials in the present invention can be also obtained by the optical resolution of the reaction product of racemic trans- or cis-stilbene oxide with alkyl glycinate or alaninate. (support)

The supports, used in the present invention, are organic or inorganic compounds such as polystyrene, polyamides, polyacrylates, polymethacrylates, silica-gel, almina, and glass beads. Moreover, mixtures and composites of these materials, and reaction products with other elements can be used as a support.

The supports are preferably used in the form of particles, the size of which is 0.1 to 1000 micrometer, preferably 1 to 100 micrometer. Supports which are microporous with a large total area are preferable, and suitable pore sizes are 10 Å to 10000 Å. However, a suitable ratio of pore size to particle size is less than 1/10.

The separating agent of the present invention can be produced by fixing, chemically or physically, one of the optically active carboalkylated amino alcohols with a support through, or not through, a spacer.

The amount of the optically active compound may be 0.1 to 100 w/w% of the support, preferably 1 to 10 w/w%.

Specific methods are described below.

Optically active carboalkylated amino alcohols, which are characteristic in the present invention, are prepared as described before. These optically active materials are preferred to have high optical purity but are not necessarily to be pure.

Moreover, as described below, to fix the optically active material chemically on the support, a variety of synthetic processes can be applied. Therefore, the method for the preparation of the optically active part is not restricted only to those mentioned before.

A spacer is an agent combining the support and the optically active material in the present invention.

For example, when an inorganic support such as silica-gel, alumina, and glass beads is used as a support, many kinds of silane coupling reagents can be used. Moreover, the following spacers can also be used; materials which have more than two reactive functions and can react without damaging the optical activity of the optical active compounds represented by general formulae (2-1), (2-2), (2-3), and (2-4); and monofunctional materials which have comparatively intensive interaction with the support and can react without the damage mentioned above. As the reactive functions in the multifunctional spacers, carboxylic acid, carboxylic anhydride, acyl halide, ester, halide, and epoxide functions are satisfactory. Aldehyde and imine functions are also applicable. Moreover, monocarboxylic acids, monohalides, and monoepoxides having an aliphatic long chain are effective as a monofunctional spacer.

The methods for the chemical fixation of the optically active compounds represented by above mentioned general formulae (2-1), (2-2), (2-3), and (2-4), on the support are as follow.

One of the methods is the direct fixation of the optically active compounds on silica-gel, treated with a silane coupling reagent, or on an organic polymer having a reactive functional group. For example, when the support has an epoxy group, the amino group in the optically active compounds can react with the support by ring-opening. The acylation of the amino group with carboxylic acids or their derivatives, the alkylation of the amino group with halides, the tosylation of the amino group with tosyl halides, and the carbamoylation of the amino group with isocyanates are also useful to fix the optically active compounds on the support. A typical example is shown in the following reaction scheme (4). After carboalkylation of (1S,2R)-2-amino-1,2-diphenylethanol with ethyl bromoacetate, the ester part is converted to the sodium salt with aq. sodium hydroxide. Then, the salt is allowed to react with the glycidyl group of silica-gel treated with 3-glycidoxypropyltrimethoxysilane. The product is changed to the corresponding copper salt.

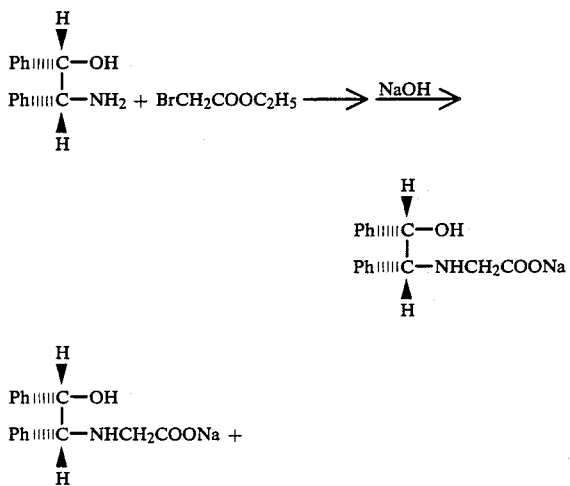

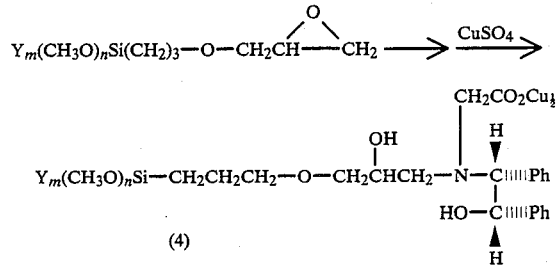

(4)

[wherein Ph represents a phenyl group, Y represents silica-gel, m and n is an integer, m+n is 3]

In another method, an inorganic support is allowed to react with the silane coupling reagent bonded previously with one of the optically active compounds represented by the general formulae (2-1), (2-2), (2-3) and (2-4).

Moreover, separating agents can be prepared by the homo- or co-polymerization of polymerizable compounds bonded previously with one of the optically active compounds represented by the general formulae (2-1), (2-2), (2-3), and (2-4). The examples of the polymerizable parent compounds are p-(chloromethyl)styrene, glycidyl acrylate, glycidyl methacrylate, acrylic acid and its derivatives, and methacrylic acid and its derivatives.

Moreover, to fix the above mentioned optically active compounds on an inorganic support or on an organic polymer support, the reaction steps can be reversed. Namely, in the first step, the amino group of 2-amino1,2-diphenylethanol is allowed to react with a spacer, a support, or a polymerizable compound. Then, the reaction product is alkylated with a carboalkylating agent such as ethyl bromoacetate and ethyl 2-chloropropionate. In the third step, the product of the second step is converted to a metallic salt.

For example, (1S,2R)-2-amino-1,2-diphenylethanol is allowed to react with 3-glycidoxypropyl-trimethoxysilane. After N-alkylation with ethyl bromo-acetate, the ester part is converted to a sodium salt with aq. sodium hydroxide. The salt is combined with silica-gel by chemical reaction and converted to a copper salt. The reaction steps are presented in scheme (5).

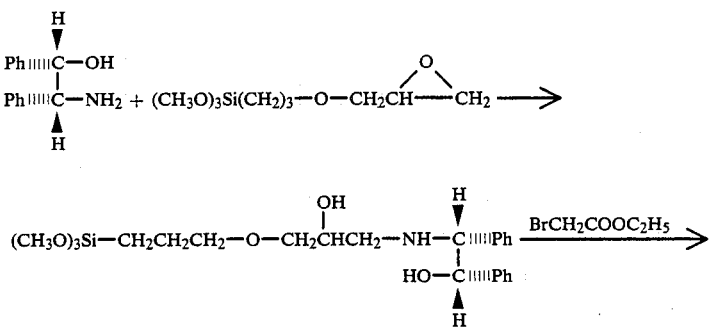

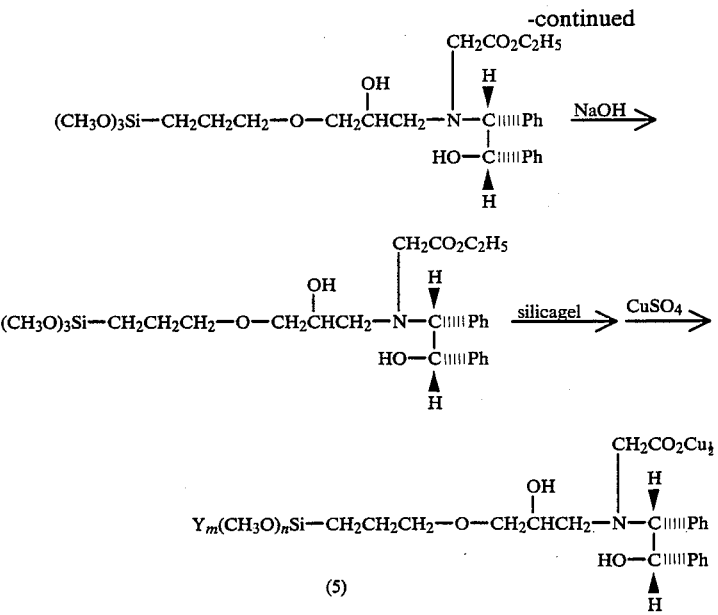

[wherein Ph represents a phenyl group, Y represents silica-gel, m and n is an interger and m+n is 3]

The method for the physical fixation of the optically active compounds on the support is as follows.

A hydrophobic group as a long chain alkyl such is introduced into the optically active compounds represented by above mentioned general formulae (2-1), (2-2), (2-3) and (2-4), and the modified compounds are adsorbed on silica-gel or activated carbon given a hydrophobic nature, or on an organic polymer having a hydrophobic group.

The optically active separating agents are applicable for the optical resolution by chromatography such as gas chromatography, liquid chromatography, and thin layer chromatography.

With respect to application to liquid chromatography or thin layer chromatography, all solvents except for those which can dissolve the separating agent and/or to react with it, can be used as an eluent. Moreover, there is no limitation, except for reactive liquids, in the case of the separating agent, in which the optically active compound is fixed chemically with the support or is insoluabilized by cross-linking. But, it is preferable to check many kinds of eluents because the resolving ability of the separating agent changes depending on the eluent.

EXAMPLES

The following examples illustrate preferred embodiments of the present invention, which by no means limit the invention.

Capacity factor (K'), separation factor ($\alpha$) and resolution factor (Rs) are calculated according to the following equetions, respectively.

$$\text{capacity factor } (K') = \frac{[(\text{retention time}) - (\text{dead time})]}{\text{dead time}}$$

separation factor ($\alpha$) =

$$\frac{\text{capacity factor for the enantiomer adsorbed more strongly}}{\text{capacity factor for the enantiomer adsorbed more weakly}}$$

resolution factor (Rs) =

$$2 \times \frac{\text{distance between two peaks}}{\text{the sums of the band width of the both peaks}}$$

EXAMPLE 1 synthesis of (1R,2S)-2-ethoxycarbonylmethyl-amino-1,2-diphenylethanol (1R,2S)-2-amino-1,2-diphenylethanol (2.10 g) was dissolved in dichloromethane (30 ml) and stirred at room temperature. Ethyl bromoacetate (2.00 g), dissolved in dichloromethane (15 ml), was added to the solution. The mixture was stirred at room temperature for 7 days, and then triethylamine (1.5 ml) was added and stirred at room temperature for an additional day. After the spot of the starting material in TLC disappeared, dichloromethane was evaporated under reduced pressure Benzene (100 ml) was added to the remaining residue, and the triethylamine hydrobromide salt was washed out with water. The organic layer was washed with brine and dried over anhydrous sodium sulfate. The solution was filtered and evaporated. The residue (2.60 g, 88%) was recrystallized from hexane (ca. 300 ml). The crystals deposited were collected and dried under reduced pressure. Yield 2.20 g (75%); mp 123-125° C.; $[\alpha]_D^{18} +2.4°$ (c 1.00, EtOH). IR (KBr): 3180, 1745, 765, 705 cm−1. $^1$H-NMR (CDCl$_3$): 1.17 (t, 3H, J =7 Hz), 2.35 (bs, 2H), 3.16 (pseudo s, 2H), 3.98 (q, 2H, J =7 Hz), 4.15 (d, 1H, J =6 Hz), 4.76 (d, 1H, J =6 Hz), 7.20 (s, 10H) ppm.

Analytically calculated for $C_{18}H_{21}NO_3$: C, 72.22; H, 7.07; N, 4.68. Found: C, 72.43; H, 7.11; N, 4.47.

EXAMPLE 2 synthesis of (1S,2R)-2-ethoxycarbonylmethyl-amino-1,2-diphenylethanol (1S,2R)-2-amino-1,2-diphenylethanol (3.15 g) was dissolved in dichloromethane (45 ml) and stirred at room temperature. Ethyl bromoacetate (3.0 g), dissolved in dichloromethane (15 ml), was added to the solution. The mixture was stirred at room temperature for 7 days, and then triethylamine (2.31 ml) was added and stirred at room temperature for an additional day. After the spot of the starting material in TLC disappeared, dichloromethane was evaporated under reduced pressure. Benzene (100 ml) was added to the remaining residue, and the triethylamine hydrobromide salt was washed out with water. The organic layer was washed with brine and dried over anhydrous sodium sulfate. The solution was filtered and evaporated. The residue (3.41 g, 77%) was recrystallized from hexane (ca. 300 ml). The crystals deposited were collected and dried under reduced pressure. Yield 3.25 g (73%); mp 126.5-127 ° C.; $[\alpha]D^{22} -2.5°$ (c 1.01, EtOH). IR and $^1$H-NMR spectra, and Rf value of the product are completely identical with those of (1R,2S)-form mentioned in Example 1.

EXAMPLE 3 synthesis of (1S,2R)-2-carboxymethylamino-1,2-diphenylethanol mono sodium salt (1S,2R)-2-ethoxycarbonylmethylamino-1,2-diphenylethanol (2.02 g) was suspended in methanol (20 ml), and 1 M sodium hydroxide (6.8 ml) was added with stirring. After the suspension was stirred at room temperature for 3 days, the precipitate was completely dissolved. The solution was evaporated and dried in vacuo (about 2 mm Hg )at 70 ° C for 12h. Yield 1.92 g (97%), mp 229~234° C. (decomp.), $[\alpha]D^{16} -3.7$ (c 0.76, $H_2O$). IR (KBr): 3280, 1600, 1415, 760, 700 $cm^{-1}$.

EXAMPLE 4 synthesis of (1R,2S)-2-carboxymethylamino-1,2-diphenylethanol mono sodium salt (1R,2S)-2-ethoxycarbonylmethylamino-1,2-diphenylethanol (2.60 g) was suspended in methanol (20 ml), and 1 M sodium hydroxide (8.6 ml) was added with stirring. After the suspension was stirred at room temperature for 3 days, the precipitate was completely dissolved. The solution was evaporated and dried in vacuo (about 2 mm Hg) at 70 ° C. for 12 h. Yield 2.47 g (97%), mp 231-235 ° C. (decomp.), $[\alpha]D^{17} +3.8°$ (c 0.83, $H_2O$). IR (KBr): 3280, 1600, 1415, 760, 700 $cm^{-1}$.

EXAMPLE 5 synthesis of (1S,2R)-2-carboxymethylamino-1,2-diphenylethanol 1.55 g of (1S,2R)-2-carboxymethylamino-1,2-diphenylethanol mono sodium salt was dissolved in 40 ml of water and 1.2 M hydrochloric acid was added to adjust the pH at 8. The precipitated crystals were washed 2 times with water and 2 times with methanol. The washed crystals were dried under reduced pressure (about 2 mm Hg) at 70 ° C. for 12 h. Mp 250-251.5 ° C. (decomp.); $[\alpha]D^{21} -3.4°$ (c 1.00, 1H NaOH) IR (KBr): 3320, 3050, 2890, 1625, 1570, 1390, 760, 710, 700 $cm^{-1}$.

Analytically calculated for $C_{16}H_{17}NO_3$:C, 70.83; H, 6.32; N, 5.16. Found: C, 70.54; H, 6.14; N, 5.05.

EXAMPLE 6 synthesis of (1R,2S)-2-carboxymethylamino-1,2-diphenylethanol 2.50 g of (1R,2S)-2-carboxymethylamino-1,2-diphenylethanol mono sodium salt was dissolved in 60 ml of water and 1.2 M hydrochloric acid was added to adjust the pH at 8. The precipitated crystals were washed 2 times with water and 2 times with methanol. The washed crystals were dried under reduced pressure (about 2 mm Hg) at 70 ° C. for 12 h. Yield 1.95 g (84%); mp 249-251 ° C. (decomp.); $[\alpha]D^{21} +3.3$ (c 1.00, 1M NaOH). IR (KBr): 3320, 3050, 2890, 1625, 1570, 1390, 760, 710, 700 $cm^{-1}$ (the spectum is identical with that of (1S,2R)-form).

EXAMPLE 7 synthesis of (1S,2S)-2-ethoxycarbonylmethylamino-1,2-diphenylethanol (1S,2S)-2-amino-1,2-diphenylethanol (526 mg) was dissolved in dichloromethane (10 ml) and stirred at room temperature. Ethyl bromoacetate (412 mg), dissolved in dichloromethane (3 ml), was added to the solution. The mixture was stirred at room temperature for 5 days, and then triethylamine (0.4 ml) was added and stirred at room temperature for an additional day. After the spot of the starting material in TLC disappeared, dichloromethane was evaporated under reduced pressure. Benzene (100 ml) was added to the residue, and the solution was worked up. The crude product (2.9 g) was purified by silica gel column chromatography using dichloromethane/ methanol (19/1) as an eluent, to give the pure product as oil. Yield 614 mg (83%); $[\alpha]D^{17} -33.8°$ (c 1.03, MeOH). IR (neat): 3350, 1740, 1205, 765, 705 $cm^{-1}$. $^1$H-NMR ($CDCl_3$): 1.20 (t, 3H, J =7 Hz), 3.02 (bs, 2H), 3.66 (d, 1H, J =8 Hz), 4.07 (q, 2H, J =7 Hz), 4.59 (d, 1H, J =8 Hz), 7.05 (s, 10H) ppm.

Analytically calculated for $C_{18}H_{21}NO_3$: C, 72.22; H, 7.07; N, 4.68. Found: C, 72.48; H, 7.21; N, 4.42.

EXAMPLE 8 synthesis of (1S,2S)-2-carboxymethylamino-1,2-diphenylethanol mono sodium salt (1S,2S)-2-ethoxycarbonylmethylamino-1,2-diphenylethanol (450 mg) was dissolved in methanol (10 ml), and 1 M sodium hydroxide (1.6 ml) was added with stirring. The mixture was stirred at room temperature for 12 h, and then evaporated and dried in vacuo (about 2 mm Hg) at 70 ° C. for 12 h. Yield 421 mg (96%); mp 222-225 ° C. (decomp.); $[\alpha]D^{18} -43.3°$ (c 1.06, MeOH). IR (KBr): 3305, 1590, 1415, 770, 700 $cm^{-1}$.

EXAMPLE 9 synthesis of (1S,2S)-2-carboxymethylamino-1,2-diphenylethanol 296 mg of (1S,2S)-2-carboxymethylamino-1,2diphenylethanol mono sodium salt was suspended in 50 ml of water, and 1.2 M hydrochloric acid was added to adjust the pH at 8.

After the solution was stirred for 2 hours, precipitated crystals were filtered and washed 2 times with water to give 213 mg (79%) of crude (1S, 2S)-2-carboxymethylamino-1,2-diphenylethanol.

The crude crystals were recrystallized from water, and 167 mg (62%) of (1S,2S)-2-carboxymethylamino-1,2-diphenylethanol was obtained. Mp 226–228° C. (decomp.); $[\alpha]D-52.1°$ (c 1.02, 1 M NaOH/MeOH=1/1). IR (KBr): 3270, 3120, 1610, 1385, 1075, 765, 705 cm$^{-1}$.

Analytically calculated for $C_{16}H_{17}NO_3$: C, 70.83; H, 6.32; N, 5.16. Found: C, 70.59; H, 6.21; N, 5.32.

EXAMPLE 10

Production of a separating agent combined with (1R,2S)-2-carboxymethylamino-1,2-diphenylethanol mono sodium salt To a suspension of 7.0 g of silica-gel, Lichrosorbs:100, a tradename of the product being available from E. Merck, having a size of 10 microns, having dried for 3 h at 120° C. in 50 ml of dry benzene, 3.5 ml of 3-glycidoxypropyltrimethoxysilane was added. Then the suspension was refluxed for 8 h with removal of methanol formed from the mixture. After cooling, the benzene was removed by filtration, and the silica-gel was suspended in methanol (20 ml). Then, the mono sodium salt of (1R,2S)-2-carboxymethylamino-1,2-diphenylethanol obtained in Example 4 was added. The mixture was shaken for 3 days at the room temperature. The silica-gel was collected by filtration, washed with methanol and poured into a copper (II) sulfate solution. The copper-loaded chiral separating agent was collected by filtration and washed successively with water and the mobile phase. A possible structure of the obtained chiral separating agent is shown below.

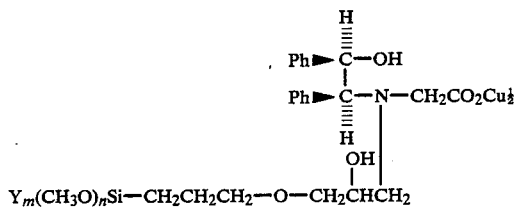

EXAMPLE 11

Example 10 was followed except that (1S,2S)-2-carboxymethylamino-1,2-diphenylethanol mono-sodium salt obtained in Example 8 was instead used. A possible structure of the obtained chiral separating agent is shown below.

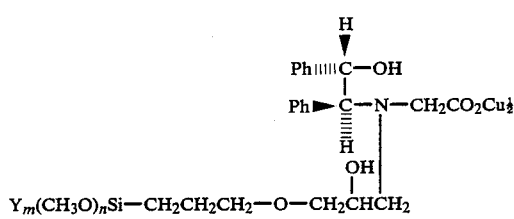

EXAMPLE 12

Example 10 was followed except that (1S,2R)-2-carboxymethylamino-1,2-diphenylethanol mono-sodium salt obtained in Example 3 was instead used. A possible structure of the obtained separating agent is below shown.

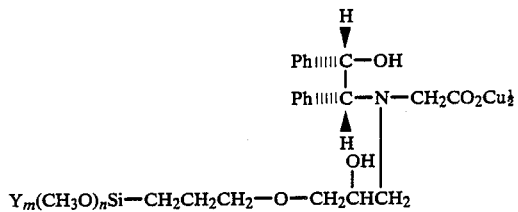

EXAMPLE 13

The separating agent obtained in Example 10 was packed into a stainless steel of a column having a length of 25 cm and an internal diameter of 0.46 by the ascending slurry method.

The chromatography was taken at 30° C. at a flow rate of 1.00 ml per minute, using a 0.25 mM solution of copper (II) sulfate as the mobile phase. Results in the resolution of amino acids, amino acid derivatives and hydroxy acids are shown in Table 1.

EXAMPLE 14

The resultion was carried out in the same way as in Example 13, instead using the separating agent obtained in Example 11. Results are shown in Table 2.

EXAMPLE 15

A separating agent was prepared, using (1R,2R)-2-amino-1,2-diphenylethanol, in the same way as shown in Examples 7, 8 and 11. A possible structure of the obtained separating agent is shown below.

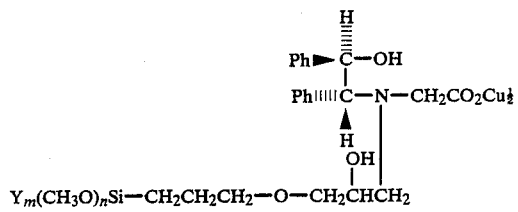

TABLE 1

| racemic compound | capacity factor | | separation factor | resolution factor |
|---|---|---|---|---|
| | $K'_d$ | $K'_l$ | $\alpha$ | $R_s$ |
| DL- leucine | 10.4 | 14.4 | 1.35 | 1.83 |
| DL- methionine | 11.3 | 13.6 | 1.21 | 1.25 |
| DL- arginine hydrochloride | 10.9 | 13.6 | 1.25 | 1.50 |
| DL- alanine | 6.24 | 7.61 | 1.22 | 1.36 |
| DL- glutamine | 8.13 | 10.1 | 1.24 | 1.53 |
| DL- glutamic acid | 8.86 | 11.1 | 1.25 | 0.84 |
| DL- citrulline | 9.24 | 11.7 | 1.27 | 1.54 |
| DL- ornitine hydrochloride | 8.03 | 9.84 | 1.23 | 0.99 |
| DL- proline | 8.08 | 18.0 | 2.22 | 3.49 |
| DL- lysine hydrochloride | 7.81 | 9.73 | 1.25 | 1.16 |
| DL- tyrosine | 12.2 | 10.3 | 1.19 | 1.20 |
| DL- tryptophane | 19.6 | 16.4 | 1.19 | 1.25 |
| DL- mandelic acid | 3.52 | 4.43 | 1.26 | 0.91 |
| DL- N-acetyl tryptophane | 4.29 | 5.00 | 1.17 | — |
| DL- N-CBZ-phenylalanine | 8.77 | 11.4 | 1.30 | — |
| DL- lactic acid | 3.13 | 4.32 | 1.38 | — |
| DL- indolinic acid* | 25.1 | 38.4 | 1.53 | 3.00 |
| DL- tropic acid** | 6.08 | 7.34 | 1.21 | 1.38 |
| DL- phenylalaninic | — | — | — | 1.45 |

TABLE 1-continued

| racemic compound | capacity factor $K'_d$ | $K'_l$ | separation factor $\alpha$ | resolution factor $R_s$ |
|---|---|---|---|---|
| acid amide | | | | |

*Flow rate 1.5 ml/minute (at 50° C.)

**Flow rate 0.8 ml/minute (at 40° C.)

TABLE 2

| racemic compound | capacity factor $K'_d$ | $K'_l$ | separation factor $\alpha$ | resolution factor $R_s$ |
|---|---|---|---|---|
| DL- threonine | 5.89 | 7.71 | 1.31 | 1.74 |
| DL- tyrosine | 12.0 | 9.87 | 1.22 | — |
| DL- phenylalanine | 11.1 | 9.80 | 1.22 | — |
| DL- citrulline | 9.40 | 10.02 | 1.09 | — |
| DL- aspartic acid | 4.34 | 5.04 | 1.16 | — |
| DL- serine | 5.48 | 6.36 | 1.16 | — |
| DL- indolinic acid* | 17.14 | 28.5 | 1.66 | 2.31 |
| DL- tropic acid** | 2.35 | 3.51 | 1.49 | 1.60 |

*Flow rate 1.5 ml/minute (at 50° C.)

**Flow rate 0.8 ml/minute (at 40° C.)

What is claimed is:

1. An optically active carboalkylated amino alcohol isomer having one of the formulae (1-1), (1-2), (1-3) and (1-4):

$$\begin{array}{c}\text{H}\\\text{Ph}\blacktriangleright\overset{|}{\underset{|}{\text{C}}}-\text{OH}\\\text{Ph}\blacktriangleright\overset{|}{\underset{\overline{\text{H}}}{\text{C}}}-\text{NH}-\overset{|}{\underset{\text{R}}{\text{CH}}}-\overset{\text{O}}{\overset{\|}{\text{C}}}\text{XZ}\end{array} \quad (1\text{-}1)$$

$$\begin{array}{c}\text{H}\\\text{Ph}\text{\tiny{IIII}}\overset{|}{\underset{|}{\text{C}}}-\text{OH}\\\text{Ph}\text{\tiny{IIII}}\overset{|}{\underset{\text{H}}{\text{C}}}-\text{NH}-\overset{|}{\underset{\text{R}}{\text{CH}}}-\overset{\text{O}}{\overset{\|}{\text{C}}}\text{XZ}\end{array} \quad (I\text{-}2)$$

$$\begin{array}{c}\text{H}\\\text{Ph}\blacktriangleright\overset{|}{\underset{|}{\text{C}}}-\text{OH}\\\text{Ph}\text{\tiny{IIII}}\overset{|}{\underset{\text{H}}{\text{C}}}-\text{NH}-\overset{|}{\underset{\text{R}}{\text{CH}}}-\overset{\text{O}}{\overset{\|}{\text{C}}}\text{XZ}\end{array} \quad (1\text{-}3)$$

$$\begin{array}{c}\text{H}\\\text{Ph}\text{\tiny{IIII}}\overset{|}{\underset{|}{\text{C}}}-\text{OH}\\\text{Ph}\blacktriangleright\overset{|}{\underset{\overline{\text{H}}}{\text{C}}}-\text{NH}-\overset{|}{\underset{\text{R}}{\text{CH}}}-\overset{\text{O}}{\overset{\|}{\text{C}}}\text{XZ}\end{array} \quad (1\text{-}4)$$

in which Ph is phenyl, R is hydrogen, an alkyl having 1 to 10 carbon atoms or an aryl having 6 to 10 carbon atoms, X is [a group of] —O— or —S—, and Z is hydrogen, an alkyl having 1 to 10 carbon atoms or a metal element selected from the group consisting of copper iron, zinc, nickel, cobalt, magnesium, calcium, sodium or potassium.

2. An optically active carboalkylated amino alcohol as claimed in claim 1, in which R is hydrogen, X is —O— and Z is hydrogen, methyl, ethyl, copper iron, zinc, nickel, cobalt, magnesium, calcium, sodium or potassium.

* * * * *

UNITED STATES PATENT AND TRADEMARK OFFICE
CERTIFICATE OF CORRECTION

PATENT NO. : 4,966,985
DATED : October 30, 1990
INVENTOR(S) : Masaki HASEGAWA et al It is certified that error appears in the above-identified patent and that said Letters Patent is hereby corrected as shown below:

Column 14, line 30; delete "[a group of]".
          line 32; after "copper" insert a comma.
          line 37; after "copper" insert a comma.

Signed and Sealed this

Ninth Day of June, 1992

Attest:

DOUGLAS B. COMER

*Attesting Officer*    *Acting Commissioner of Patents and Trademarks*